(12) United States Patent
Yamamoto (10) Patent No.: US 8,221,572 B2
(45) Date of Patent: Jul. 17, 2012

(54) MANUFACTURING METHOD FOR ABSORPTIVE ARTICLE

(75) Inventor: Hiroki Yamamoto, Kanonji (JP)

(73) Assignee: Uni-Charm Corporation, Ehime (JP)

( * ) Notice: Subject to any disclaimer, the term of this patent is extended or adjusted under 35 U.S.C. 154(b) by 92 days.

(21) Appl. No.: 12/390,068

(22) Filed: Feb. 20, 2009

(65) Prior Publication Data
US 2009/0320993 A1    Dec. 31, 2009

(30) Foreign Application Priority Data

Jun. 25, 2008 (JP) ................. P2008-165293

(51) Int. Cl.
*B32B 29/00* (2006.01)
(52) U.S. Cl. ............ 156/176; 156/276; 156/229
(58) Field of Classification Search ............. 156/276
See application file for complete search history.

(56) References Cited

U.S. PATENT DOCUMENTS

| | | | | |
|---|---|---|---|---|
| 6,336,543 | B1 * | 1/2002 | Thomas | 193/37 |
| 6,387,471 | B1 * | 5/2002 | Taylor et al. | 428/152 |
| 2004/0123954 | A1 * | 7/2004 | Yoneoka et al. | 156/494 |
| 2006/0185135 | A1 * | 8/2006 | Yamamoto et al. | 28/116 |

FOREIGN PATENT DOCUMENTS

| | | | |
|---|---|---|---|
| JP | 2002273808 A | * | 9/2002 |
| JP | 2006-141642 A | | 6/2006 |

* cited by examiner

*Primary Examiner* — Khanh P Nguyen
*Assistant Examiner* — Margaret Squalls
(74) *Attorney, Agent, or Firm* — Lowe, Hauptman, Ham & Berner, LLP (57) ABSTRACT

A manufacturing method for an absorptive article according to the present invention includes: placing a continuum of the elastic members 4A and 5A in a desired layout, on at least one surface of a web 7A being transported continuously, while swinging the continuum of the elastic members 4A and 5A in a direction crossing a moving direction of the web 7A; feeding the web 7A on which the continuum of the elastic members 4A and 5A are placed, between a first roll 8, which is rotating in the moving direction, and a second roll 9; and pressing the continuum of the elastic members 4A and 5A, and the web 7A between the first roll 8 and the second roll 9. A recess 20 is formed in a predetermined pattern on at least an outer peripheral surface of the first roll 8, and the continuum of the elastic members 4A and 5A, and the web 7A are pressed between the first roll 8 and the second roll 9 while the continuum of the elastic members 4A and 5A placed in an area 3A corresponding to the crotch portion on one surface of the web 7A faces the recess 20 formed on the outer peripheral surface of the first roll 8.

17 Claims, 6 Drawing Sheets

MANUFACTURING METHOD FOR ABSORPTIVE ARTICLE

CROSS REFERENCE TO RELATED APPLICATIONS

This application is based upon and claims the benefit of priority from the prior Japanese Patent Application No. JP 2008-165293, filed on Jun. 25, 2008; the entire contents of which are incorporated herein by reference.

BACKGROUND OF THE INVENTION

1. Field of the Invention

The present invention relates to a manufacturing method for an absorptive article including a leg opening portion and a crotch portion and having an elastic member disposed extending from the leg opening portion to the crotch portion.

2. Description of the Related Art

There has heretofore been known a manufacturing method for a disposable diaper having a web laminate in which a first elastic member and a second elastic member are sandwiched and bonded, in a predetermined curved shape, between a first web and a second web. (See Japanese Patent Application Publication No. 2006-141642, for example.)

In such a manufacturing method, the above-mentioned web laminate is formed in the following manner. Specifically, a continuum of the first elastic member and a continuum of the second elastic member are placed, each in a desired layout, between the first web and a second web each coated with an adhesive, while being swung in a direction (hereinafter, a CD direction) crossing a moving direction (hereinafter, an MD direction). Then, the continuum of the first elastic member and the continuum of the second elastic member are sandwiched and pressed between nip rolls thereby to be bonded to the first web and the second web.

SUMMARY OF THE INVENTION

Generally, in the above-mentioned manufacturing method for a disposable diaper, the first elastic member and the second elastic member are disposed in an undesired locus in the crotch portion when they are disposed in accordance with the shape of the leg opening portion. As a result, stresses are developed in the widthwise and the lengthwise directions of the disposable diaper, and the absorber is caused to deform, thereby inducing a leak. Therefore, the stresses on the first elastic member and the second elastic member in the crotch portion need to be reduced.

Figure 1:
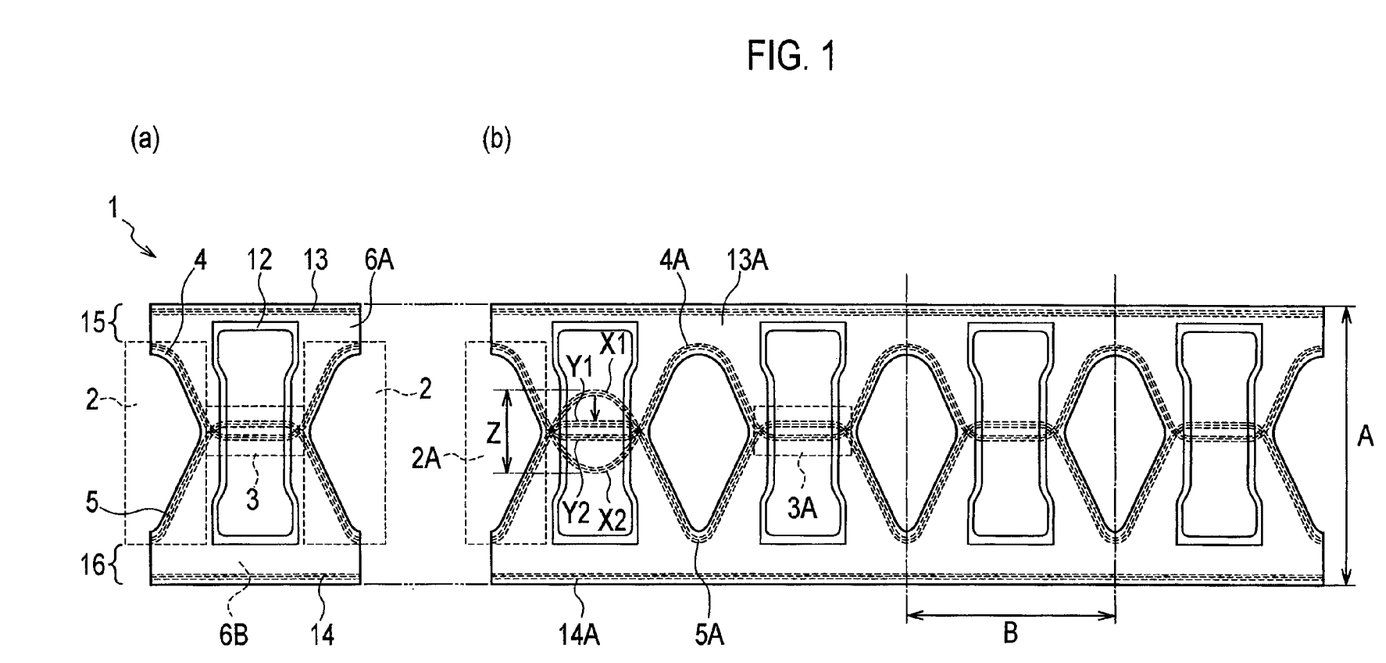
FIGS. 1A and 1B are expanded views of an absorptive article manufactured by a manufacturing method according to a first embodiment of the present invention.

It is therefore desired that, as shown in FIGS. 1A and 1B, a continuum 4A of the first elastic member and a continuum 5A of the second elastic member placed in a region 3A corresponding to a crotch portion 3 be displaced, by their respective restoring forces, from the positions X1 and X2 (at which the continuums of the first and second elastic members are placed between a first web 7A and a second web 7B) to the positions Y1 and Y2 (at which they are as nearly parallel to the MD direction of the first web 7A and the second web 7B as possible) (hereinafter referred to be as aligned positions).

However, in the above-mentioned manufacturing method, the continuum of the first elastic member and the continuum of the second elastic member are pressed between the nip rolls immediately after being placed in the desired layout between the first web and the second web, which are coated with the adhesive. Accordingly, the method has the following problem. In other words, the continuum 4A of the first elastic member and the continuum 5A of the second elastic member placed in the region 3A corresponding to the crotch portion 3 will be bonded to the first web and the second web while remaining in the positions X1 and X2, prior to being displaced to the aligned positions Y1 and Y2.

The present invention has therefore been made in consideration of the above-described problems inherent in the related art. It is an object of the present invention to provide a manufacturing method for an absorptive article, which can properly bond the elastic member to the web, in the region corresponding to the crotch portion.

A first aspect of the present invention is summarized as a manufacturing method for an absorptive article provided with a leg opening portion and a crotch portion and having an elastic member disposed extending from the leg opening portion to the crotch portion. The manufacturing method includes: placing a continuum of the elastic member in a desired layout, on at least one surface of a web being transported continuously, while swinging the continuum of the elastic member in a direction crossing a moving direction of the web; feeding the web on which the continuum of the elastic member is placed, between a first roll, which is rotating in the moving direction, and a second roll; and pressing the continuum of the elastic member and the web between the first roll and the second roll. A recess is formed in a predetermined pattern on at least an outer peripheral surface of the first roll, and the continuum of the elastic member and the web are pressed between the first roll and the second roll while the continuum of the elastic member placed in an area corresponding to the crotch portion on one surface of the web faces the recess formed on the outer peripheral surface of the first roll.

As described above, the present invention can provide the manufacturing method for an absorptive article, which can properly bond the elastic member to the web, in the region corresponding to the crotch portion.

DETAILED DESCRIPTION OF THE PREFERRED EMBODIMENTS

A Manufacturing Method According to a First Embodiment of the Present Invention Description will be given with reference to FIGS. 1A to 6 with regard to the manufacturing method according to the first embodiment of the present invention.

FIG. 1A is an expanded view of an absorptive article 1 manufactured by the manufacturing method according to the first embodiment of the present invention. FIG. 1B is an expanded view of the absorptive article 1 in the process of being manufactured by the manufacturing method according to the first embodiment of the present invention.

Note that, the absorptive article 1 manufactured by the manufacturing method according to the first embodiment of the present invention may be a pants-type disposable diaper or an open-type disposable diaper.

As shown in FIG. 1A, the absorptive article 1 manufactured by the manufacturing method according to the first embodiment of the present invention includes a liquid-permeable top sheet 6A, a liquid-impermeable back sheet 6B, and an absorber 12 disposed between the top sheet 6A and the back sheet 6B.

The absorptive article 1 is provided with leg opening portions 2, a crotch portion 3, a front waistband portion 15, and a rear waistband portion 16.

Here, the absorptive article 1 includes one or more first elastic member 4 and one or more second elastic member 5 disposed extending from the leg opening portion 2 to the crotch portion 3. The first and second elastic members 4 and 5 form a leg gather. The leg gather is disposed along an opening portion in the leg opening portion 2. Note that, the absorptive article 1 may be configured to include only any one of the first and second elastic members 4 and 5 disposed extending from the leg opening portion 2 to the crotch portion 3.

Also, the absorptive article 1 includes one or more third elastic members 13 disposed in the front waistband portion 15, and one or more fourth elastic members 14 disposed in the rear waistband portion 16. The third and fourth elastic members 13 and 14 form a waist gather.

Description will be given below with reference to FIGS. 1A to 6 with regard to the manufacturing method for the absorptive article 1 according to the first embodiment of the present invention. Specifically, in the manufacturing method for the absorptive article 1 according to the first embodiment of the present invention, description will be given with regard to a step of forming the leg gather to be disposed in the leg opening portion 2 of the absorptive article 1.

Figure 2:
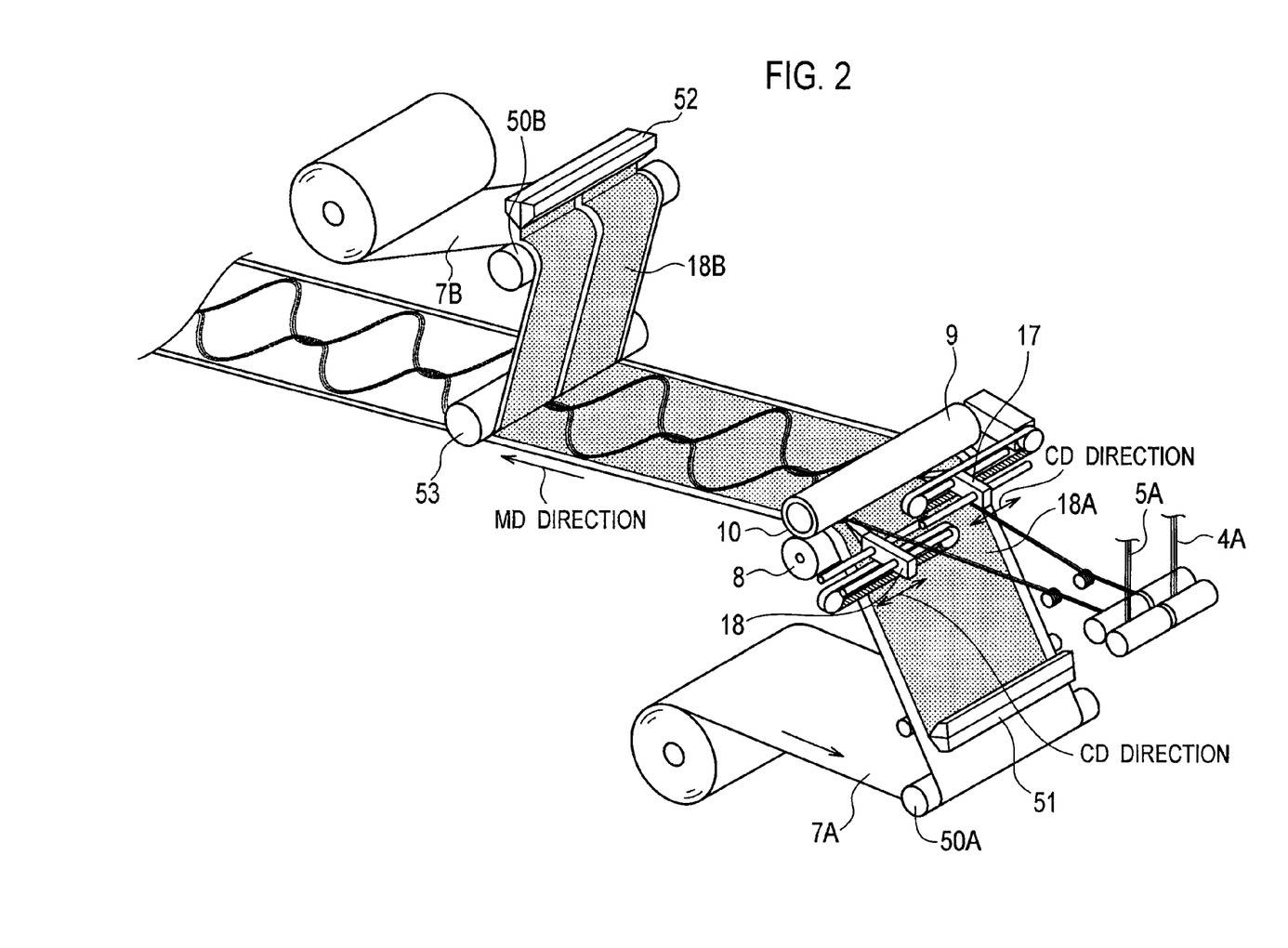
FIG. 2 is a perspective view illustrating the manufacturing method according to the first embodiment of the present invention.
Figure 3:
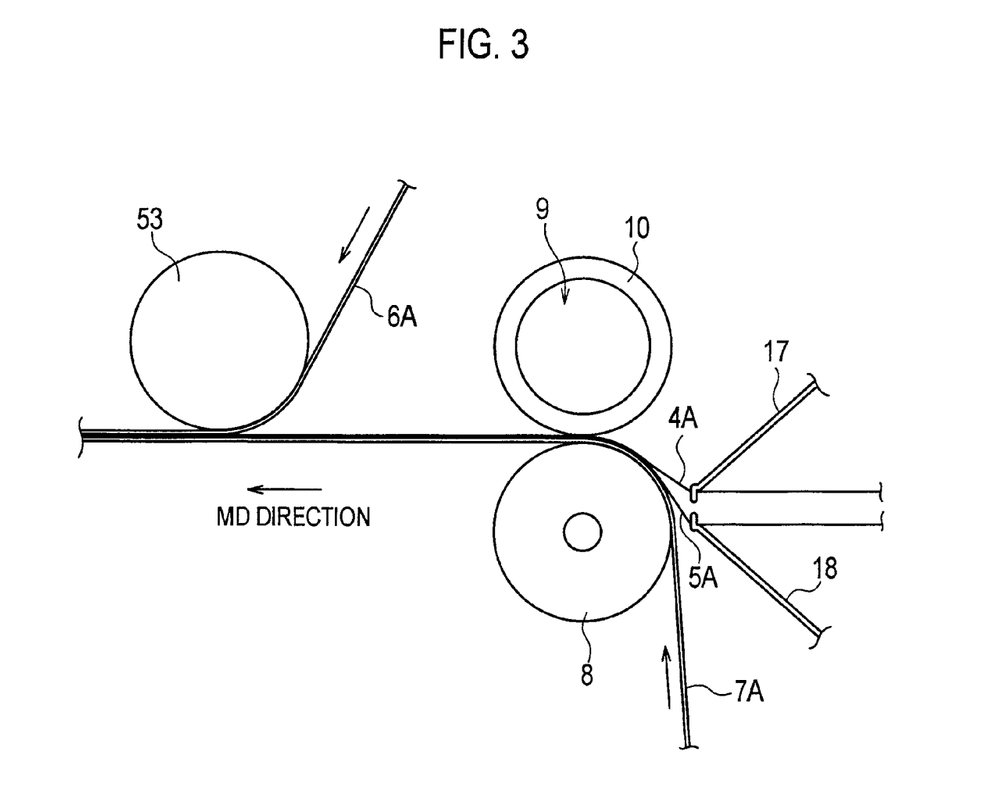
FIG. 3 is a side view illustrating the manufacturing method according to the first embodiment of the present invention.

Note that, in this manufacturing method, a first web 7A is continuously transported. Further, the width direction (or CD direction) of a first web 7A corresponds to the lengthwise direction of the absorptive article 1, and the lengthwise direction (or MD direction) of the first web 7A corresponds to the width direction of the absorptive article 1. As shown in FIGS. 2 and 3, in a first step, an raw fabric of the first web unrolls to dispense the first web 7A therefrom, and turns the first web 7A around to change its direction by a guide roll 50A.

In a second step, an adhesive coating apparatus 51 applies a coating of an adhesive 18A to a surface of the first web 7A facing a second web 7B, at its predetermined location.

In a third step, by a first swinging guide 17 and a second swinging guide 18, respectively, a continuum 4A of the first elastic member and a continuum 5A of the second elastic member are placed in a desired layout on at least one surface of the first web 7A coated with the adhesive 18A, while swinging the continuum 4A of the first elastic member and the continuum 5A of the second elastic member in the CD direction of the first web 7A (that is, a direction crossing its moving direction).

Here, the desired layout of the first elastic member 4 (that is, the continuum 4A of the first elastic member) may be different from the desired layout of the second elastic member 5 (that is, the continuum 5A of the second elastic member).

In a fourth step, placing the first web 7A on which the continuum 4A of the first elastic member and the continuum 5A of the second elastic member are fed, between a first roll 8, which is rotating in the MD direction, and a second roll 9, so that the continuum 4A of the first elastic member, the continuum 5A of the second elastic member, and the first web 7A can be pressed between the first roll 8 and the second roll 9.

In a fifth step, an adhesive coating apparatus 52 applies a coating of an adhesive 18B to a surface of the second web 7B, on the surface facing the first web 7A, at its predetermined location. Here, the second web 7B is dispensed by unrolling an raw fabric of the second web 7B.

In a sixth step, by a roll 53, the surface of the first web 7A on which the continuum 4A of the first elastic member and the continuum 5A of the second elastic member are bonded, and the surface of the second web 7B on which the adhesive 18B is applied, are bonded.

In this manner, the continuum 4A of the first elastic member and the continuum 5A of the second elastic member that form the leg gather can be disposed between the first web 7A and the second web 7B.

Figure 4:
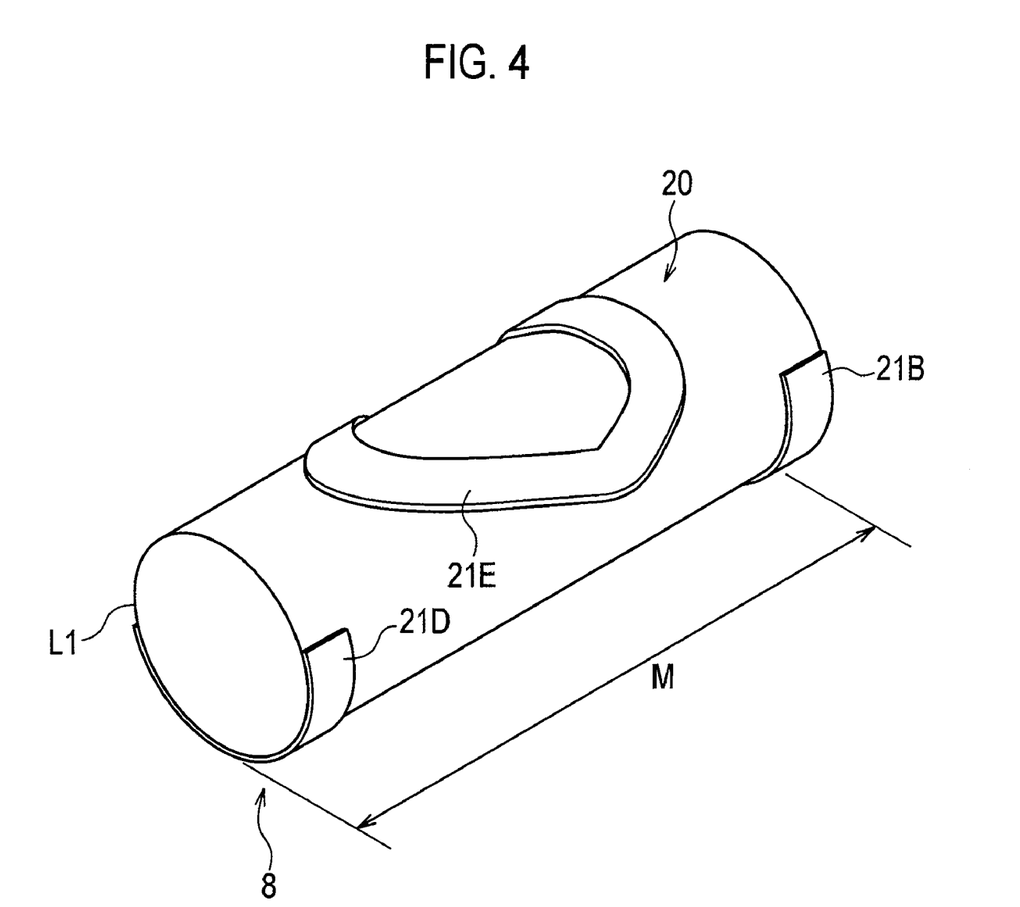
FIG. 4 is a perspective view of a first roll used in the manufacturing method according to the first embodiment of the present invention.

Here, as shown in FIG. 4, a recess 20 is formed in a predetermined pattern on the outer peripheral surface of the first roll 8. Note that, regions other than the recess 20 on the outer peripheral surface of the first roll 8 will be hereinafter called as projections 21A to 21E.

In the above fourth step, the continuum 4A of the first elastic member, the continuum 5A of the second elastic member, and the first web 7A are sandwiched and pressed between the first roll 8 and the second roll 9 so that, the continuum 4A of the first elastic member and the continuum 5A of the second elastic member placed in a region 3A corresponding to the crotch portion on the one surface of the first web 7A faces the recess 20 formed in the outer peripheral surface of the first roll 8. Also, on the one surface of the first web 7A, the continuum 4A of the first elastic member and the continuum 5A of the second elastic member placed in a region 2A corresponding to the leg opening portion faces the projection 21E formed on the outer peripheral surface of the first roll 8.

This makes it is possible to avoid the continuum 4A of the first elastic member and the continuum 5A of the second elastic member placed in the region 3A corresponding to the crotch portion 3, from being bonded to the first web and the second web while remaining in the positions X1 and X2 (at which the continuums 4A and 5A are placed between the first web and the second web 7A and 7B) prior to being displaced to the aligned positions Y1 and Y2.

In other words, according to the above-described manufacturing method, the first continuum 4A of the first elastic member and the second continuum 5A of the second elastic member, which are placed in the region 2A corresponding to the leg opening portion, can be bonded to the first web and the second web, while remaining in the positions X1 and X2. Further, the first continuum 4A of the first elastic member and the second continuum 5A of the second elastic member can be bonded to the first web and the second web after being changed into the aligned positions Y1 and Y2.

Figure 5:
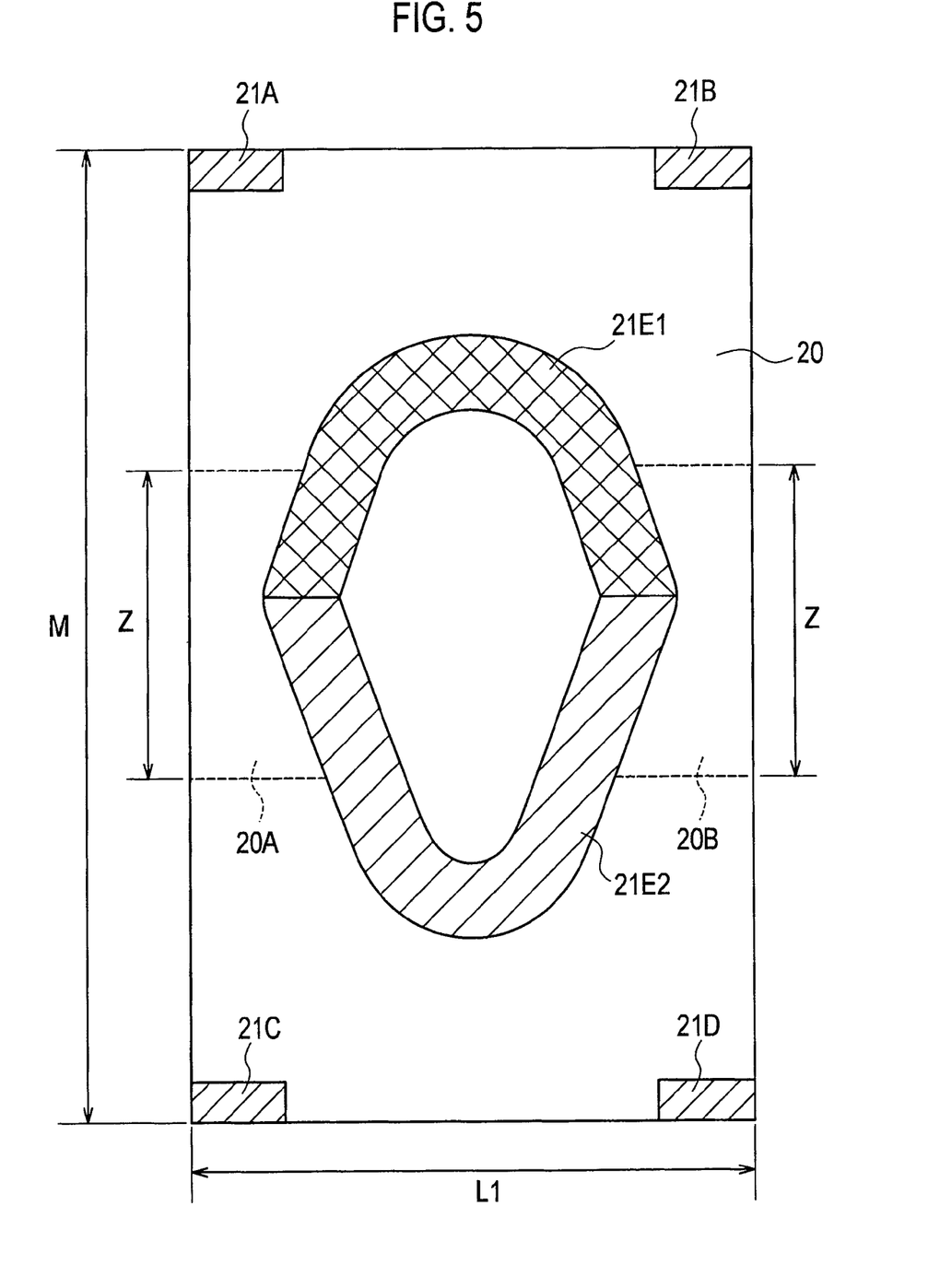
FIG. 5 is an expanded view of the first roll used in the manufacturing method according to the first embodiment of the present invention.
Figure 6:
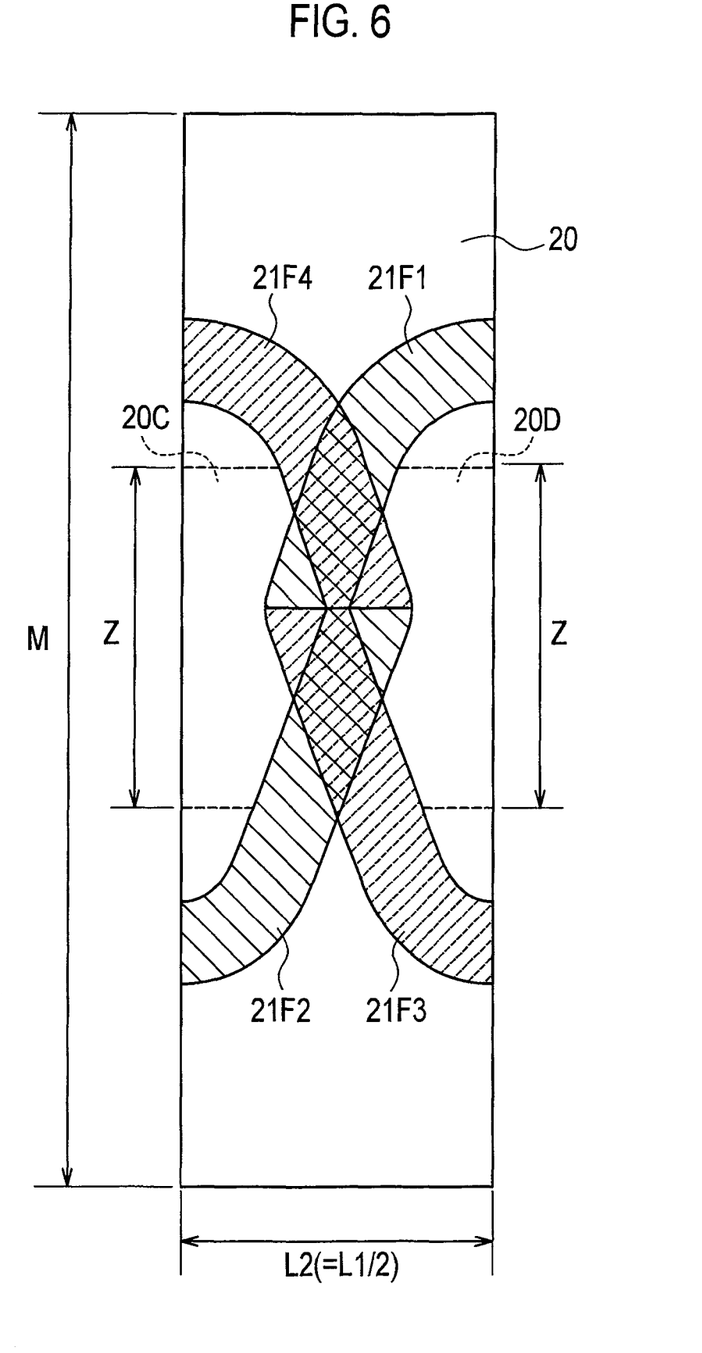
FIG. 6 is an expanded view of the first roll used in the manufacturing method according to the first embodiment of the present invention.

Referring to FIGS. 5 and 6, the first roll 8 is illustrated in the expanded view by way of example.

In FIG. 5, an example is shown in which the outer peripheral length L1 of the first roll 8 is substantially equal to the width B of the absorptive article (that is, the pitch distance between products in the MD direction of the first web 7A).

In the example shown in FIG. 5, an upper half 21E1 of the projection 21E is a portion facing the continuum 4A of the first elastic member, and a lower half 21E2 of the projection 21E is a portion facing the continuum 5A of the second elastic member.

Note that, region 20A and 20B on the outer peripheral surface of the first roll 8 have the recess 20 formed therein, since these regions are portions facing the continuum 4A of the first elastic member and the continuum 5A of the second elastic member placed in the region 3A corresponding to the crotch portion 3.

More specifically, the continuum 4A of the first elastic member and the continuum 5A of the second elastic member that are placed on the region 3A corresponding to the crotch portion 3 need to face the recess 20 formed in the outer peripheral surface of the first roll 8, whether the continuum 4A of the first elastic member and the continuum 5A of the second elastic member are in the positions X1 and X2 or positions Y1 and Y2 in FIG. 1B.

Therefore, the region 20A and 20B on the outer peripheral surface of the first roll 8 are formed so that the width of the region 20A and 20B in the CD direction is greater than the distance between the continuum 4A of the first elastic member in the position X1 and the continuum 5A of the second elastic member in the position X2.

In other words, the recess 20 may be formed in any pattern on the outer peripheral surface of the first roll 8, provided only that the recess 20 is formed in the region 20A and 20B as mentioned above.

Also, the projections 21A to 21D are provided in order for the first and roll 8 and the second roll 9 to stably press the continuums therebetween. Here, the projections 21A and 21B or the projections 21C and 21D may be formed integrally with or separate from each other on the outer peripheral surface of the first roll 8.

On the other hand, in FIG. 6, an example is shown in which the outer peripheral length L1 of the first roll 8 is substantially half the width B of the absorptive article 1 (that is, the pitch distance between products in the MD direction of the first web 7A).

In the example shown in FIG. 6, the first roll 8 makes two revolutions in order to press the continuum 4A of the first elastic member and the continuum 5A of the second elastic member placed in a product pitch in the MD direction of the first web 7A.

In the meantime, a portion of the first roll 8 facing the continuum 4A of the first elastic member shifts in the order of; a projection 21F1, a recess 20C, a recess 20D, and a projection 21F4. Meanwhile, a portion of the first roll 8 while facing the continuum 5A of the second elastic member shifts in the order of: a projection 21F3, the recess 20C, the recess 20D, and a projection 21F2.

Note that, the regions 20C and 20D on the outer peripheral surface of the first roll 8 have the recess 20 formed therein, since these regions are the portions facing the continuum 4A of the first elastic member and the continuum 5A of the second elastic member placed in the region 3A corresponding to the crotch portion 3.

In other words, the recess 20 may be formed in any pattern on the outer peripheral surface of the first roll 8, provided only that the recess 20 is formed in the regions 20C and 20D.

Also, the outer peripheral surface of the first roll 8 may be provided with the projections 21A to 21D (not shown) in order for the first roll 8 and the second roll 9 to stably press the continuums therebetween.

Note that, it may be configured that the first roll 8 is a driven roll and the second roll 9 is a non-driven roll. Alternatively, it may be configured that both of the first roll 8 and the second roll 9 are driven rolls.

Also, the recess 20 may be formed in the predetermined pattern on the outer peripheral surface of the second roll 9, as in the case of the outer peripheral surface of the first roll 8.

Also, an anti-adhesion process may be applied on the outer peripheral surface of the second roll 9, in order to prevent the adhesive 18A which is coated on the first web 7A, from adhering onto the outer peripheral surface of the second roll 9.

For example, the anti-adhesion process on the outer peripheral surface of the second roll 9 can be performed by covering the outer peripheral surface of the second roll 9 with a second non-adhesive member 10. Here, the second non-adhesive member 10 is replaceable. As an example of the anti-adhesion process, the silicone rubber or the like may be used. Further, as an example of the second non-adhesive member 10, an adhesive tape having an anti-adhesive process, or the like may be used.

Also, the anti-adhesion process may be likewise applied on the outer peripheral surface of the first roll 8. For example, the anti-adhesion process on the outer peripheral surface of the first roll 8 can be performed by covering the outer peripheral surface of the first roll 8 with a first non-adhesive member. Here, the first non-adhesive member is replaceable Also, the above-described manufacturing method may further include a step of cooling the second roll 9. Here, it is preferable that the thickness of the above-mentioned second non-adhesive member 10 be less than the thickness of the above-mentioned first non-adhesive member in order to improve the effect of cooling of the second roll 9.

Operations and Effects of the Absorptive Article
According to the First Embodiment of the Present
Invention According to the absorptive article of the first embodiment of the present invention, the recess 20 is formed so as to face the region 3A corresponding to the crotch portion 3 on the outer peripheral surface of the first roll 8. Accordingly, the continuum 4A of the first elastic member and the continuum 5A of the second elastic member placed in the region 2A corresponding to the leg opening portion 2 can be bonded to the first web and the second web, while remaining in the positions at which the continuums 4A and 5A are placed between the first web and the second web 7A and 7B. Further, the continuum 4A of the first elastic member and the continuum 5A of the second elastic member placed in the region 3A corresponding to the crotch portion 3 can be bonded to the first web and the second web, after being displaced to their aligned positions Y1 and Y2.

According to the absorptive article of the first embodiment of the present invention, the outer peripheral length of the first roll 8 may be shorter than the width B of the absorptive article 1. Thereby, the first swinging guide 17 and the second swinging guide 18 can be brought close to a point in which the first roll 8 and the second roll 9 are pressed to each other, and thus, the desired layout can be arranged in a form close to the locus of the first swinging guide 17 and the second swinging guide 18.

According to the absorptive article according to the first embodiment of the present invention, the second roll 9 may be the non-driven roll thereby to accommodate the changes in the peripheral speed of the first roll 8 and the second roll 9 caused by the wearing of the first roll 8 and the second roll 9.

According to the absorptive article of the first embodiment of the present invention, the first roll 8, that is the roll having the recess 20 formed therein, may be the driven roll. This makes it possible to eliminate a misalignment between the predetermined pattern of the recess 20 and the desired layout of the placement of the continuum 4A of the first elastic member and the continuum 5A of the second elastic member.

According to the absorptive article of the first embodiment of the present invention, the manufacturing method may include the step of cooling the second roll 9. This makes it possible to achieve the effect of hardening the adhesive 18A coated on the first web 7A, and the effect of allowing heat to escape from the adhesive 18A.

In other words, on the first web 7A, the adhesive 18A that is coated on the portion facing recess 20 is not cooled, thereby taking a long time to be hardened. Meanwhile, the adhesive 18A that is coated on the portion facing the projection 21 is cooled, thereby taking a short time to be hardened. Accordingly, the continuum 4A of the first elastic member and the continuum 5A of the second elastic member are easily displaced to the aligned positions Y1 and Y2.

According to the absorptive article of the first embodiment of the present invention, the anti-adhesion process may be applied on the outer peripheral surface of the second roll 9. Accordingly, the adhesive 18A coated on the first web 7A can be prevented from adhering onto the outer peripheral surface of the second roll 9.

According to the absorptive article of the first embodiment of the present invention, the thickness of the above-mentioned second non-adhesive member 10 may be less than the thickness of the above-mentioned first non-adhesive member. Accordingly, the above-mentioned effect of cooling the second roll 9 can be further improved.

According to the absorptive article of the first embodiment of the present invention, the anti-adhesion process on the outer peripheral surface of the second roll 9 may be performed by covering the outer peripheral surface of the second roll 9 with the second non-adhesive member 10, which is replaceable. Thereby, when the outer peripheral surface of the second roll 9 is worn out, it only needs to replace the second non-adhesive member 10, and the second roll 9 in itself does not need to be replaced. Accordingly, the cost for replacing the second roll 9 in itself can be reduced.

In other words, when the second roll 9 is a flat roll having no recess formed therein, it is not required to replace the outer peripheral surface of the roll having the recess 20 formed therein, such as the first roll 8.

Modified Examples

In the above-mentioned embodiment, the first web 7A and the second web 7B are bonded together, after the first web 7A is bonded with the continuum of the first elastic member 4A and the continuum of the second elastic member 5A and second elastic member, respectively. However, the present invention is not limited to the foregoing.

The leg gather may be formed for example by performing the following steps.

In a first step, the raw fabric of the first web is unrolled to dispense the first web 7A therefrom, and the first web 7A is turned around to change its direction by the guide roll 50A. At the same time, the raw fabric of the second web is also unrolled to dispense the second web 7B therefrom, and the second web 7B is turned around to change its direction by a guide roll 50B.

In a second step, the adhesive coating apparatus 51 applies a coating of the adhesive 18A to the surface of the first web 7A facing the second web 7B, at its predetermined location. At the same time, the adhesive coating apparatus 52 applies a coating of the adhesive 18B to the surface of the second web 7B facing the first web 7A, at its predetermined location.

In a third step, the continuum 4A of the first elastic member is placed in the desired layout on the surface of the first web 7A coated with the adhesive 18A, while the continuum 4A of the first elastic member is swung by the first swinging guide 17, in the CD direction of the first web 7A (that is, the direction crossing its moving direction). At the same time, the continuum 5A of the second elastic member is placed in the desired layout on the surface of the second web 7B coated with the adhesive 18B, while the continuum 5A of the second elastic member is swung by the second swinging guide 18, in the CD direction of the second web 7B (that is, the direction crossing its moving direction).

Here, the desired layout of the first elastic member 4 (that is, the continuum 4A of the first elastic member) may be different from the desired layout of the second elastic member 5 (that is, the continuum 5A of the second elastic member).

In a fourth step, the first web 7A on which the continuum 4A of the first elastic member is placed thereon and the second web 7B on which the continuum 5A of the second elastic member is placed are placed between the first roll 8, which is rotating in the MD direction, and the second roll 9, so that the continuum 4A of the first elastic member, the continuum 5A of the second elastic member, the first web 7A, and the second web 7B can be sandwiched and pressed between the first roll 8 and the second roll 9.

In this manner, the continuum 4A of the first elastic member and the continuum 5A of the second elastic member, which form the leg gather, can be disposed between the first web 7A and the second web 7B.

While the invention has been described in detail above with reference to the above-mentioned embodiments, it should be apparent to those skilled in the art that this invention is not limited to the embodiments described herein. The invention may be practiced in the form of modifications and variations without departing from the basic concept and scope of the invention as defined in the appended claims. It is to be therefore understood that the disclosure herein is for purposes of illustration only and is not intended to limit the scope of the invention.

What is claimed is:

1. A method of manufacturing an absorptive article provided with that includes a pair of leg opening portions, a crotch portion between the pair of leg opening portions in a transverse direction of the absorptive article, and an elastic member extending between the leg opening portions across the crotch portion, said method comprising:

placing a continuum of the elastic member in a desired layout, on a surface of a web being transported continuously in a machine direction, while swinging the continuum of the elastic member in a cross direction crossing the machine direction;

feeding the web on which the continuum of the elastic member is placed, between a first roll, which is rotating in the machine direction, and a second roll; and pressing and bonding the continuum of the elastic member to the web between the first roll and the second roll, wherein said first roll has a recess formed in a predetermined pattern on an outer peripheral surface of the first roll, and a non-recess region formed on the outer peripheral surface of the first roll, said recess and non-recess region arranged sequentially in the machine direction as the first roll rotates, and wherein
said recess is arranged corresponding to the continuum of the elastic member placed in a first area corresponding to the crotch portion on said surface of the web;

said non-recess region arranged corresponding to the continuum of the elastic member placed in a second area corresponding to at least one of the leg opening portions on said surface of the web, and the continuum of the elastic member and the web are pressed between the first roll and the second roll, so that the continuum of the elastic member placed in the first area corresponding to the crotch portion on said surface of the web faces the recess on the outer peripheral surface of the first roll and is therefore not bonded to the web in the first area.

2. The method according to claim 1, wherein an outer peripheral length of the first roll is substantially half of a width of the absorptive article in the machine direction.

3. The method according to claim 1, wherein the first roll is a driven roll, and the second roll is a non-driven roll.

4. The manufacturing method according to claim 1, further comprising:

applying adhesive to said surface of the web before feeding said web between the first and second rolls, and cooling the second roll for hardening the adhesive on the web.

5. The method according to claim 1, wherein an outer peripheral surface of the second roll is non-adherable to the web.

6. The method according to claim 5, wherein the outer peripheral surface of the second roll is covered with a non-adhesive member which is replaceable.

7. The method according to claim 6, wherein the outer peripheral surface of the first roll is covered with another non-adhesive member which is replaceable, and a thickness of the non-adhesive member is less than a thickness of said another non-adhesive member.

8. The method according to claim 1, wherein the continuum of elastic member includes a first elastic element and a second elastic element, the layout in which the first elastic element is placed on said web different from that of the second elastic element, in said pressing and bonding, the first elastic element and the second elastic element placed in the first area corresponding to the crotch portion on the surface of the web faces the recess formed on the outer peripheral surface of the first roll and therefore are not bonded to the web in the first area, and the first elastic member and the second elastic member placed in the second area corresponding to at least one of the leg opening portions on the surface of the web face the non-recess region formed on the outer peripheral surface of the first roll and therefore are bonded to the web in the second area.

9. The method according to claim 1, wherein the continuum of the elastic member and the web are pressed between the first roll and the second roll so that the continuum of the elastic member placed in the second area corresponding to said at least one leg opening portion on said surface of the web faces the non-recess region on the outer peripheral surface of the first roll and therefore is bonded to the web in the second area.

10. The method according to claim 1, wherein the continuum of the elastic member placed in the first area corresponding to the crotch portion is moved from a first configuration, in which the continuum of the elastic member is placed on said web upstream of the first and second rolls, to a second, different configuration downstream of said first and second rolls.

11. The method according to claim 10, wherein the continuum of the elastic member in the second configuration in the first area is substantially parallel to the machine direction.

12. The method according to claim 11, further comprising bonding the continuum of the elastic member in the first area and in the second configuration to the web downstream of said first and second rolls.

13. The method according to claim 1, wherein the non-recess region has a closed loop shape.

14. The method according to claim 9, wherein the non-recess region has a closed loop shape.

15. A method of manufacturing an absorptive article that includes a pair of leg opening portions, a crotch portion between the pair of leg opening portions in a transverse direction of the absorptive article, and an elastic member extending between the leg opening portions across the crotch portion, said method comprising:

placing a continuum of the elastic member in a desired layout, on a surface of a web being transported continuously in a machine direction, while swinging the continuum of the elastic member in a cross direction crossing the machine direction;

feeding the web on which the continuum of the elastic member is placed, between a first roll, which is rotating in the machine direction, and a second roll; and pressing and bonding the continuum of the elastic member to the web between the first roll and the second roll, wherein said first roll has a recess formed in a predetermined pattern on an outer peripheral surface of the first roll, and a non-recess region formed on the outer peripheral surface of the first roll, said recess and non-recess region arranged sequentially in the machine direction as the first roll rotates, and wherein said recess is arranged corresponding to the continuum of the elastic member placed in a first area corresponding to the crotch portion on said surface of the web;

said non-recess region arranged corresponding to the continuum of the elastic member placed in a second area corresponding to at least one of the leg opening portions on said surface of the web, the continuum of the elastic member and the web are pressed between the first roll and the second roll so that the continuum of the elastic member placed in the first area corresponding to the crotch portion on said surface of the web faces the recess on the outer peripheral surface of the first roll and is therefore not bonded to the web in the first area and displaced in the cross direction on the web downstream of the first and second rolls, and an outer peripheral length of the first roll is shorter than a width of the absorptive article in the machine direction.

16. The method according to claim 8, wherein in said pressing and bonding, the first elastic element and the second elastic element cross each other in the first area corresponding to the crotch portion on the surface of the web, and the first elastic element and the second elastic element are displaced in the cross direction downstream of the first and second rolls to be closer to each other in the first area.

17. The method according to claim 8, wherein said pressing and bonding the first and second elastic elements further comprises bonding the first and second elastic element in the first area to the web when the first and second elastic elements are displaced on the web downstream of the first and second rolls to be substantially parallel to each other in the cross direction in the first area.

* * * * *